United States Patent [19]

Katz

[11] Patent Number: 4,627,420

[45] Date of Patent: Dec. 9, 1986

[54] NEEDLE INSERTING INSTRUMENT FOR INTERSTITIAL RADIOTHERAPY

[76] Inventor: Harry R. Katz, 10121 Darmuid Green Dr., Potomac, Md. 20854

[21] Appl. No.: 547,250

[22] Filed: Oct. 31, 1983

[51] Int. Cl.$^4$ ............................................. A61N 5/12
[52] U.S. Cl. .................................... 128/1.1; 604/57; 269/6; 401/93
[58] Field of Search ............... 128/1.2, 1.1, 92 EB, 128/330, 340; 604/57, 59; 254/18; 269/6; 401/92, 93, 94

[56] References Cited

U.S. PATENT DOCUMENTS

| | | | |
|---|---|---|---|
| 270,681 | 1/1883 | Knight | 401/92 |
| 1,406,509 | 2/1922 | Viol | 604/57 |
| 2,269,963 | 1/1942 | Wappler. | |
| 2,844,125 | 7/1958 | Wehn | 401/93 |
| 3,323,511 | 6/1967 | Holter | 128/1.2 |
| 3,674,006 | 7/1972 | Holmer. | |
| 3,854,824 | 12/1974 | Kamo | 401/94 X |
| 4,086,914 | 5/1978 | Moore. | |
| 4,167,179 | 9/1979 | Kirsch. | |
| 4,230,413 | 10/1980 | Gartner | 401/94 X |
| 4,461,280 | 7/1984 | Baumgartner | 128/1.2 |
| 4,468,146 | 8/1984 | Tabachnik | 401/92 X |

FOREIGN PATENT DOCUMENTS

| | | | |
|---|---|---|---|
| 1307934 | 9/1962 | France | 401/94 |
| 0466836 | 8/1979 | U.S.S.R. | 128/1.2 |

Primary Examiner—Kyle L. Howell
Assistant Examiner—John C. Hanley
Attorney, Agent, or Firm—Jacob Trachtman

[57] ABSTRACT

An instrument for inserting one or more hollow needles into the body for interstitial radiotherapy of malignant tumors, which permits the incremental advancement of a needle by means of a reciprocating tubular element having a collapsible end portion which alternately grips the needle to advance it into the body, and releases the needle to permit the instrument to be moved back on the needle to a new position to again advance it further into the body. The instrument permits the insertion of a needle with only one hand, freeing the other hand to both support the area being implanted and to maintain a continuous stereotactic guidance of the advancing needle, as well as facilitating implanation of long and closely spaced needles deep within the body.

12 Claims, 6 Drawing Figures

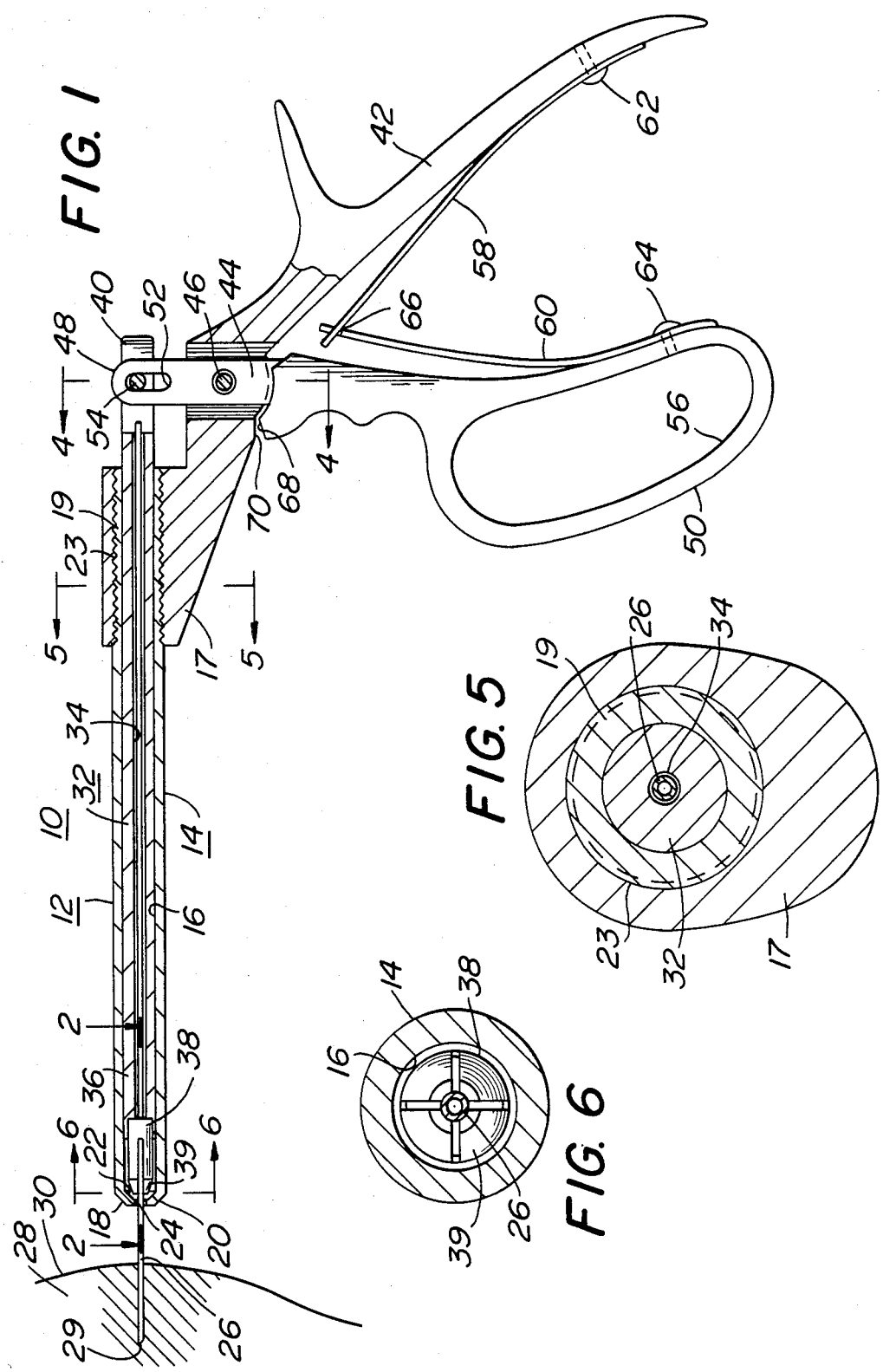

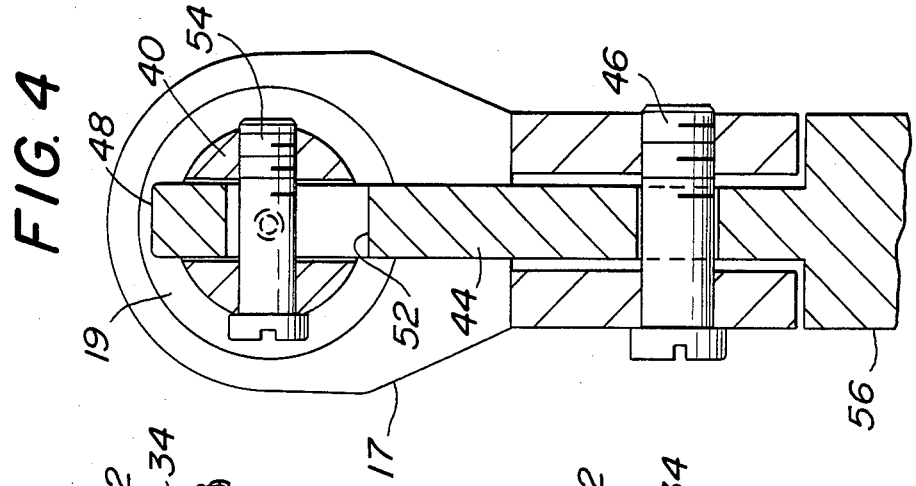
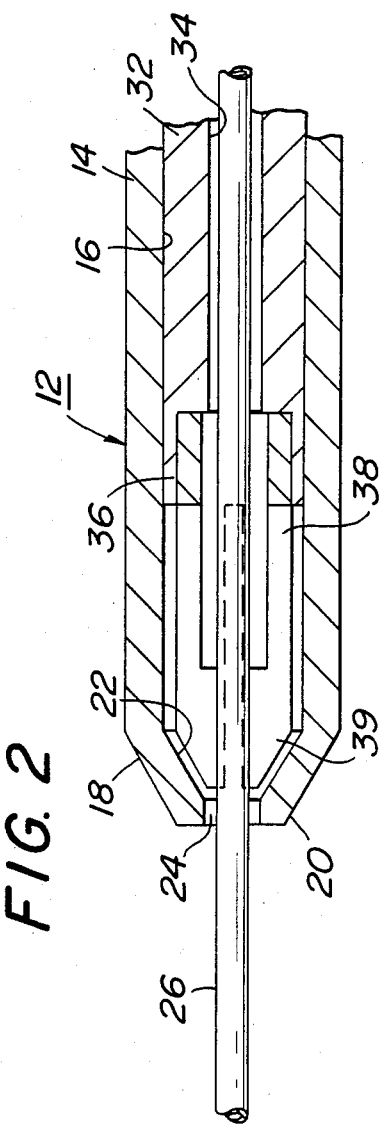

NEEDLE INSERTING INSTRUMENT FOR INTERSTITIAL RADIOTHERAPY

BACKGROUND OF THE INVENTION

The present invention relates to an instrument for use in radiotherapy, and more particularly to an instrument for inserting hollow stainless steel needles into the body during the treatment of malignant tumors by interstitial implantation of radioactive materials.

The interstitial implantation of radioactive isotopes is a well established technique for the treatment of malignant tumors. Short lengths of a radioactive source, such as Iridium-192, are linearly arranged within thin walled plastic tubes to form "ribbons." These ribbons are used as temporary interstitial implants in a wide variety of clinical situations. Each ribbon, which is very flexible, must be inserted into the body with the aid of a rigid trocar, in the form of a hollow stainless steel needle, which is sharpened at one end for piercing the skin and tumor bearing tissue. An array of the hollow needles are first inserted into the tissues to be implanted. The needles are typically spaced evenly throughout the volume of tissue to be irradiated, and are parallel to one another to avoid areas of underdose or overdose. After the hollow needles have been inserted, ribbons of radioactive sources are inserted into the bores of the needles to a position determined by the location of the tumor bearing tissue. In certain clinical situations the needles may be left in place in the body, along with the sources, for the duration of the implant, after which both are removed. In other situations, the needles may be pulled out of the body, leaving behind only the ribbon sources for the duration of the implant.

In the prior art, each needle was inserted into the body with the aid of a pin-vise which gripped the needle in a collapsible collet. This was done for several reasons. First, the needles are of a small diameter, typically 17 gauge (1.5 mm), and are very difficult to grip by hand. Second, the force needed to push even a sharp needle through the skin and connective tissue is considerable, necessitating a grip on the needle that is greater than can be obtained with the hand alone. Third, the needle must be gripped close to the point of entry into the body to avoid bending, due to its small diameter, especially when long needles, of up to 25 cms. are to be inserted. In using the standard pin-vise to grip the needle, the collet is compressed by screwing the binding nut tight with one hand while holding the handle of the pin-vise stationary with the other hand. Two hands are therefore needed to screw and unscrew the binding nut of the pin-vise in order to secure and release the collet from the needle. To fully insert an implant needle of typical length by such means, requires the repeated repositioning of the vise back along the needle as the needle is progressively pushed deeper into the body. The radiotherapist is required to alternately shift one hand from its position steadying the patient's body and feeling for the point of the needle as it approaches the intended area of the implant, to its positions for securing and releasing the pin-vise. This is awkward, time consuming, and becomes more difficult when several needles have already been inserted, leaving little room close to the needle entry area for the hands to fit in order to screw and unscrew the binding nut, especially when working deep within the body. The prior art method, which requires the removal and repositioning of the radiotherapist's hand from its position steadying the patient after each adjustment of the pin-vise, also interrupts the bimanual stereotactic guiding of the point of the needle as it passes through the tissue. A device for inserting an implant needle that does not require two hands to manually secure and release a collet by turning a threaded binding nut therefore would be of great advantage in permitting faster, easier, and smoother insertion of the needles.

SUMMARY OF THE INVENTION

Accordingly, a principal object of the invention is to provide a new and improved instrument for inserting one or more needles into the body for interstitial radiotherapy which overcomes the deficiencies of the devices previously employed.

Another object of the invention is to provide a new and improved instrument for inserting one or more needles into the body for interstitial radiotherapy which permits one-handed operation for alternately gripping and releasing an implant needle close to the point of insertion in the body.

A further object of the invention is to provide a new and improved instrument for inserting one or more needles into the body for interstitial radiotherapy which may be moved in retrograde fashion along an implant needle which is being advanced into the body, for permitting long needles to be inserted without risk of bending.

A further object of the invention is to provide a new and improved instrument for inserting one or more needles into the body for interstitial radiotherapy which permits insertion of implant needles in a closely spaced array and in areas deep within the body, by use of only one hand, especially where two-handed actuation of a needle gripping mechanism would be extremely difficult.

A further object of the invention is to provide a new and improved instrument for inserting one or more needles into the body for interstitial radiotherapy which permits continuous bimanual stereotactic guidance of a needle as it is inserted progressively deeper within the body towards its intended destination.

A further object of the invention is to provide a new and improved instrument for inserting one or more needles into the body for interstitial radiotherapy which provides for interchangeable components for allowing use of needles with different diameters and lengths.

A further object of the invention is to provide a new and improved instrument for inserting one or more needles into the body for interstitial radiotherapy having a simple design and construction, and permitting ready assembly, disassembly, cleaning and sterilization for each use.

Still other objects, features, and advantages of the invention will be apparent to those skilled in the art from the following detailed description, together with the accompanying drawings and appended claims.

The above objects as well as many others are achieved by providing an instrument comprising a unit having an elongated portion with a first end and a second end secured with a handle portion. An opening through the elongated portion receives a tubular element having a first end and a second end for reciprocating movement between first and second positions. The element has an opening for slidably receiving therein a needle to be implanted into a body. The element has means for conditionally engaging and securing the needle received therewithin when it is in its first position. Actuating means is provided for moving the element between its first and second positions.

The means for conditionally engaging and securing the needle within the element comprises a collapsible portion at the first end of the element, and a constricted region of the opening at the first end of the elongated portion of the unit. The constricted region compresses the collapsible portion of the element when it is in its first position for engaging the needle received therein, and the second end of the element is engaged by the actuating means for movement of the element between its first and second positions. The actuating means comprises a lever pivotally secured with the unit and has a first end proximate to the handle portion for manual actuation and a second end which engages the second end of the element for moving the element between its first and second positions. A spring means is provided for urging the first end of the lever in a direction away from the handle portion of the unit and moving the tubular element towards its second position, so that manual actuation of the first end of the lever towards the handle portion moves the element towards its first position for securing the needle therewithin. The elongated portion of the unit may also be detachably secured with the handle portion, while the tubular element is detachably engaged by the actuating means, so that they may be removed and interchanged with other elongated portions and elements for accommodating needles of different diameters and lengths.

DESCRIPTION OF THE DRAWING

For a fuller understanding of the nature and objects of the invention, reference should be had to the following detailed description taken in connection with the accompanying drawing, in which:

FIG. 1 is a sectional view of an instrument for inserting a hollow needle into the body for interstitial radiotherapy embodying the invention with portions in section, FIG. 2 is an enlarged sectional view taken on the line 2—2 of FIG. 1, FIG. 3 is an enlarged sectional view similar to FIG. 2 illustrating the tubular element in its first position secured with the needle received therethrough, FIG. 4 is an enlarged sectional view taken on the line 4—4 of FIG. 1, FIG. 5 is an enlarged sectional view taken on the line 5—5 of FIG. 1, and FIG. 6 is an enlarged sectional view taken on the line 6—6 of FIG. 1.

Like reference numerals designate like parts throughout the several views.

DETAILED DESCRIPTION

Referring to the figures, the instrument 10 for inserting a hollow needle into the body for interstitial radiotherapy embodying the invention, comprises a unit 12 having an elongated portion 14 with an opening 16 therethrough and a handle portion 17. The front end 18 of the elongated portion 14 has a constricted region 20 providing a sloped inner wall 22 and an opening 24 of reduced size allowing the passage therethrough of a needle 26 which is to be implanted into and through tissue 28 of a body 30.

A tubular element 32 is received within the opening 16 of the elongated portion 14 of the unit 12 for reciprocating movement between first and second positions.

The tubular element 32 has an opening 34 therethrough for movably receiving within it a needle 26 to be implanted in the body 30. The tubular element 32 is provided at its forward end 36 with a collapsible portion 38 for conditionally engaging and securing the needle 26 therewithin, and a back portion 40 for being actuated to move the tubular element within the opening 16 of the elongated portion 14 of the unit 12 between its first and second positions.

The back portion 19 of the elongated portion 14 is detachably secured with the handle portion 17 of the unit 12 by threaded means 23. The handle portion 17 has a portion 42 angularly extending from the elongated portion 14 which is adapted for being gripped by one hand. Actuating means comprising a lever 44 is pivotally secured with the handle portion 17 by a pin 46 and has a first end 48 extending upwardly towards the end 40 of the tubular element 32, and a second end 50 on the opposite side of the pivot pin 46 spaced proximately to the downwardly extending handle 42. The end 48 of the lever 44 has an elongated opening 52 which receives through it a link pin 54. The pin 54 is threadedly secured with the end 40 of the element which is split to receive the end 48 of the lever 44 therebetween. The other end 50 of the lever 44 is provided with an enlarged opening 56 for receiving the fingers of the hand which engages the handle portion 42. A first leaf spring 58 is secured at one end by a rivet 62 with the handle portion 42 while a second leaf spring 60 has an end attached by a rivet 64 to the actuating lever. The other ends of the springs 58, 60 are interengaged at 66 for urging the end 50 of the lever 44 about its pivot pin 46 in a direction away from the extending portion 42 of the handle 17. The extent of motion permitted is limited by the engagement of the surface 68 of the lever 44 with the opposite surface 70 of the handle portion 17.

The lever 44 of the actuating means is normally in its unactivated first terminal position, with its upper end 48 positioning the tubular element 32 to the right within the opening 16 of the elongating portion 14 of the unit 12 assuming its second terminal position. When the handle portion 42 and the end 50 of the actuating lever 44 of the instrument 10 are gripped by hand and compressed, the end 50 moves towards the handle portion 42, and the end 48 of the lever 44 moves the tubular element 32 to the left or in the forward direction within the opening 16 of the unit 12 and towards its first terminal position. When the tubular element 32 reaches its first terminal position, the front tapered region 39 of the collapsible portion 38 engages the region 22 of the elongated portion 14. This results in compressing the collapsible portion 38 and securing it with the needle 26 therewithin. The release of the end 50 of the lever 44 by the hand, allows it to move in the clockwise direction away from the handle portion 42 and causes the tubular element 32 to move to the right towards its second terminal position within the elongated portion 14. This releases the collapsible portion 38 of the tubular element 32 so that it is no longer secured with the needle 26.

In the use of the instrument 10, a needle 26 of appropriate length and diameter is inserted into the front of the instrument 10 through the opening 24 when the lever 44 is released, so that the collapsible portion 38 of the tubular element 32 allows the needle 26 to be received into its opening 34. With the needle 26 fully inserted into the instrument 10, a small portion having the sharpened end 29 extends therefrom. To implant the needle 26 into tissue 28, the portion 42 of the handle 17 and the end 50 of the lever 44 are gripped in one hand and squeezed to move the tubular element 32 into its first position so that the collapsible portion 38 engages the tapered wall 22 of the unit 12. The collapsible portion 38 is thereby compressed so that it firmly grips the needle 26 therewithin preventing sliding action. The point 29 of the needle 26 is positioned at a desired location on the surface of the body 30 and the instrument 10 is pushed forward to cause the needle to penetrate and enter the tissue 28 until the end 18 of the instrument 10 touches or is closely positioned to the surface of the body 30. At this time, the lever 44 is released so that the collapsible portion 38 of the tubular element 32 disengages the needle 26 and allows the instrument 10 to be slid back along the needle 26 which remains in position within the tissue 28. When the instrument 10 has been backed off a small distance, the handle 42 and lever 40 are again gripped to clamp the needle 26 within the instrument 10, allowing the needle 26 to be further advanced into the tissue. These steps are continued until the needle 26 is advanced to the desired position either partially or completely through the tissue into which it is to be implanted. A series of needles may thus be implanted in close proximity to each other by use of one hand for advancing the needle through the body, while the other hand may be positioned on the other side of the body for providing stereotactic guidance without removing such hand until the implantation has been completed.

When a needle of different length and diameter is to be implanted into the tissue, the tubular portion 14 of the unit 12 may be removed from the handle portion 17 by threadedly disengaging same. The back end 40 of the element 32 may also be disengaged from the top portion 48 of the lever 44 by removing the pin 54. The tubular portion 14 and element 32 may then be replaced with another tubular portion and complimentary tubular element of different size and length for accommodating the size and length of the desired needles which are to be implanted.

It will, of course, be understood that the description and drawing herein are illustrative merely, and that various modifications and changes may be made in the instrument disclosed without departing from the spirit of the invention.

What is claimed is:

1. An instrument for inserting a hollow needle into a body for interstitial radiotherapy comprising a unit having an elongated portion with an opening therethrough and a handle portion, a tubular element received within the opening of the unit and having an opening means for slidably receiving therein a needle to be implanted into a body, the element being movable in a linear direction along the opening of the unit between first and second positions and having means for engaging and securing against slidable movement a needle received within its opening means when the element is in its first position, and actuating means comprising a lever pivotally secured with the handle portion of the unit having a first end proximate to the handle portion for manual actuation and a second end which engages the element and is movable with the actuation of the first end of the lever for linearly moving the element between its first and second positions and normally retaining the element in its second position.

2. The instrument of claim 1 in which the means for engaging and securing the needle within the element comprises a portion of the element and a region of the opening of the elongated collapsible portion of the unit which is constricted so that it compresses the collapsible portion of the element when it is in its first position.

3. The unit of claim 2 in which the actuating means includes spring means for urging the first end of the lever in a direction away from the handle portion of the unit for moving the tubular element toward its second position, so that the manual actuation of the first end of the lever toward the handle portion of the unit moves the element toward its first position for securing therewith the needle therewithin.

4. The instrument of claim 3 in which the elongated portion of the unit is detachably secured with the handle portion and the tubular element is detachably engaged by the actuating means for being removed and interchanged with other elongated portions and elements for accommodating needles of different diameters and lengths.

5. The instrument of claim 2 in which the elongated portion of the unit has a first end and a second end, the constricted region of the unit is at the first end of the elongated portion and the second end is secured with the handle portion, the tubular element has a first end and a second end, the collapsible portion is at the first end of the element and engages the constricted region of the unit when the element is in its first position, and the second end of the element is engaged by the actuating means for movement of the element between its first and second positions.

6. The instrument of claim 5 in which the actuating means includes spring means for urging the first end of the lever in a direction away from the handle portion of the unit for moving the tubular element toward its second position, so that the manual actuation of the first end of the lever toward the handle portion of the unit moves the element toward its first position for securing therewith the needle therewithin.

7. The instrument of claim 6 in which the elongated portion of the unit is detachably secured with the handle portion and the tubular element is detachably engaged by the actuating means for being removed and interchanged with other elongated portions and elements for accommodating needles of different diameters and lengths.

8. The instrument of claim 5 in which the elongated portion of the unit is detachably secured with the handle portion and the tubular element is detachably engaged by the actuating means for being removed and interchanged with other elongated portions and elements for accommodating needles of different diameters and lengths.

9. The instrument of claim 2 in which the elongated portion of the unit is detachably secured with the handle portion and the tubular element is detachably engaged by the actuating means for being removed and interchanged with other elongated portions and elements for accommodating needles of different diameters and lengths.

10. The instrument of claim 1 in which the actuating means includes spring means for urging the first end of the lever in a direction away from the handle portion of the unit for moving the tubular element toward its second position, so that the manual actuation of the first end of the lever toward the handle portion of the unit moves the element toward its first position for securing therewith the needle therewithin.

11. The instrument of claim 10 in which the elongated portion of the unit is detachably secured with the handle portion and the tubular element is detachably engaged by the actuating means for being removed and interchanged with other elongated portions and elements for accommodating needles of different diameters and lengths.

12. The instrument of claim 1 in which the elongated portion of the unit is detachably secured with the handle portion and the tubular element is detachably engaged by the actuating means for being removed and interchanged with other elongated portions and elements for accommodating needles of different diameters and lengths.

* * * * *